(12) United States Patent
Meruelo et al.

(10) Patent No.: US 6,432,699 B1
(45) Date of Patent: Aug. 13, 2002

(54) VIRAL VECTORS HAVING CHIMERIC ENVELOPE PROTEINS CONTAINING THE IGG-BINDING DOMAIN OF PROTEIN A

(75) Inventors: Daniel Meruelo, Scarborough, NY (US); Kouichi Ohno, Kagoshima (JP)

(73) Assignee: New York University, New York, NY (US)

( * ) Notice: Subject to any disclaimer, the term of this patent is extended or adjusted under 35 U.S.C. 154(b) by 0 days.

(21) Appl. No.: 08/829,558

(22) Filed: Mar. 28, 1997

(51) Int. Cl.⁷ .............................................. C12N 15/13
(52) U.S. Cl. .................. 435/320.1; 435/69.1; 435/91.4; 435/235.1; 435/354; 435/456; 435/457; 435/476; 536/23.1; 536/23.4; 536/23.72; 424/199.1; 424/204.1; 424/218.1
(58) Field of Search ............................. 435/69.1, 320.1, 435/91.4, 456, 457, 476, 235.1, 354; 514/44; 536/23.1, 23.4, 23.72; 424/199.1, 204.1, 218.1

(56) References Cited

U.S. PATENT DOCUMENTS

| | | | |
|---|---|---|---|
| 4,863,713 A | | 9/1989 | Goodwin et al. |
| 5,091,309 A | | 2/1992 | Schlesinger et al. |
| 5,100,788 A | | 3/1992 | Lofdahl et al. |
| 5,185,440 A | | 2/1993 | Davis et al. |
| 5,217,879 A | | 6/1993 | Huang et al. |
| 5,328,985 A | | 7/1994 | Sano et al. |
| 5,591,624 A | * | 1/1997 | Barber et al. ............ 435/240.2 |
| 5,622,699 A | | 4/1997 | Ruoslahti et al. |
| 5,739,026 A | | 4/1998 | Garoff et al. |
| 5,753,499 A | | 5/1998 | Meruelo et al. |
| 5,789,245 A | | 8/1998 | Dubensky, Jr. et al. |
| 5,814,482 A | | 9/1998 | Dubensky, Jr. et al. |
| 5,834,589 A | | 11/1998 | Meruelo et al. |
| 5,843,723 A | | 12/1998 | Dubensky, Jr. et al. |
| 5,846,782 A | * | 12/1998 | Wickham et al. ........... 435/697 |
| 6,015,686 A | | 1/2000 | Dubensky, Jr. et al. |
| 6,015,694 A | | 1/2000 | Dubensky, Jr. et al. |

FOREIGN PATENT DOCUMENTS

| | | |
|---|---|---|
| WO | WO 92/10578 | 6/1992 |
| WO | WO 93/09221 | 5/1993 |
| WO | WO 93/20221 | 10/1993 |
| WO | WO 94/17813 | 8/1994 |
| WO | WO 95/07994 | 3/1995 |
| WO | WO 95/14493 | 6/1995 |
| WO | WO 95/15978 | 6/1995 |
| WO | WO 95/15979 | 6/1995 |
| WO | WO 95/27044 | 10/1995 |
| WO | WO 95/27069 | 10/1995 |
| WO | WO 95/31565 | 11/1995 |
| WO | WO 97/05266 | 2/1997 |

OTHER PUBLICATIONS

Genbank Sequence for Nilsson et al. Protein Eng. 1: 107–113, 1987.*
Surolia et al. 1982 Trends Biochem. Sci 7:74–76, 1982.*
Crystal, 1995, "Transfer of genes to humans: early lessons and obstacles to success", Science 270(5235):404–10.
Frolov et al., 1996, "Alphavirus–based expression vectors: strategies and applications", Proc Natl Acad Sci USA. 93(21):11371–7.
Kabat, 1995, "Targeting retroviral vectors to specific cells", Science 269:417.
Kasahara et al., 1994, "Tissue–specific targeting of retroviral vectors through ligand–receptor interactions", Science, 266(5189):1373–6.
Roux et al., 1989, "A versatile and potentially general approach to the targeting of specific cell types by retroviruses: application to the infection of human cells by means of major histocompatibility complex class I and class II antigens by mouse ecotropic murine leukemia virus–derived viruses", Proc Natl Acad Sci USA. 86(23):9079–83.

* cited by examiner

*Primary Examiner*—Donna Wortman
*Assistant Examiner*—Robert A. Zeman
(74) *Attorney, Agent, or Firm*—Darby & Darby

(57) ABSTRACT

The invention involves viral vectors that can be used to transduce a target cell, i.e., to introduce genetic material into the cell. The targets of interest are eukaryotic cells and particularly human cells. The transduction can be done in vivo or in vitro. More particularly the invention concerns viral vectors that have chimeric envelope proteins and contain the IgG-binding domain of protein A. These vectors when used in conjunction with antibodies targeting a particular cell are particularly useful for gene therapy.

13 Claims, 8 Drawing Sheets

Figure 1A:
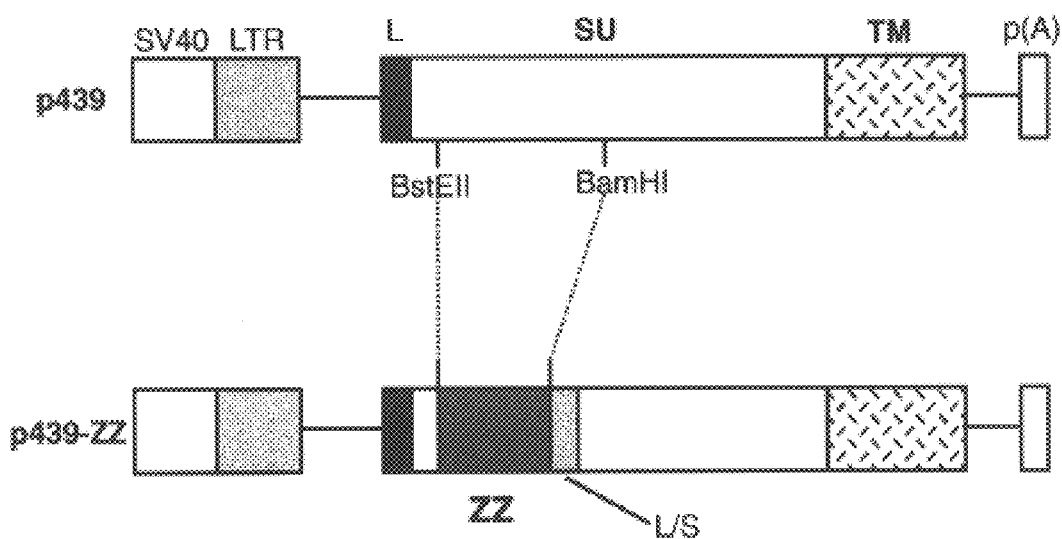

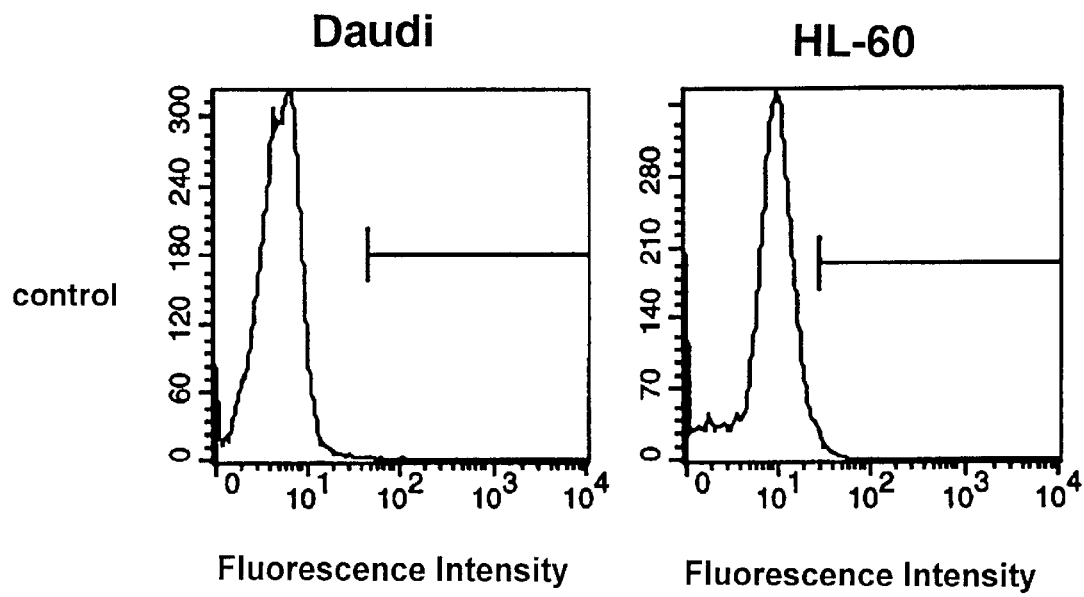
FIG. 6A  FIG. 6B
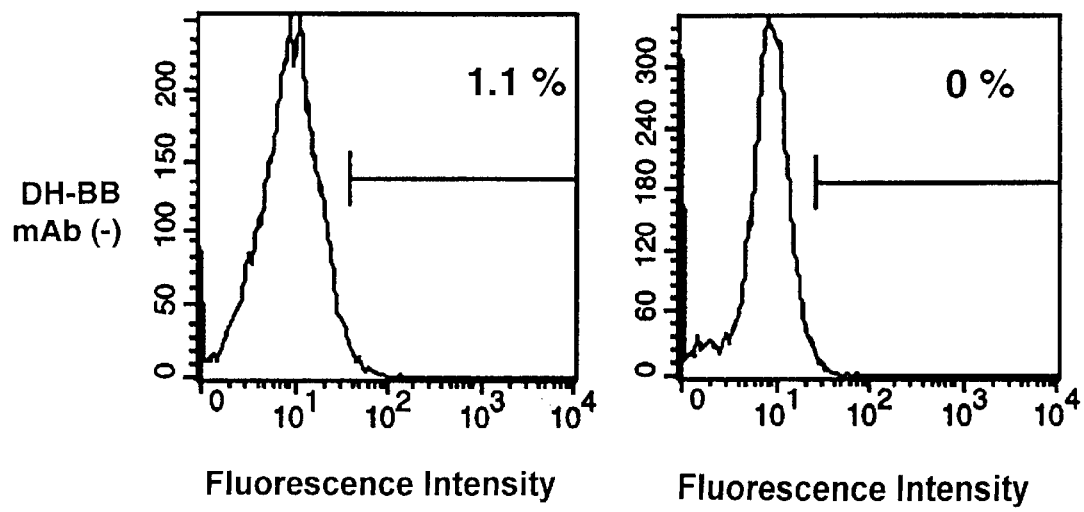
FIG. 6C  FIG. 6D

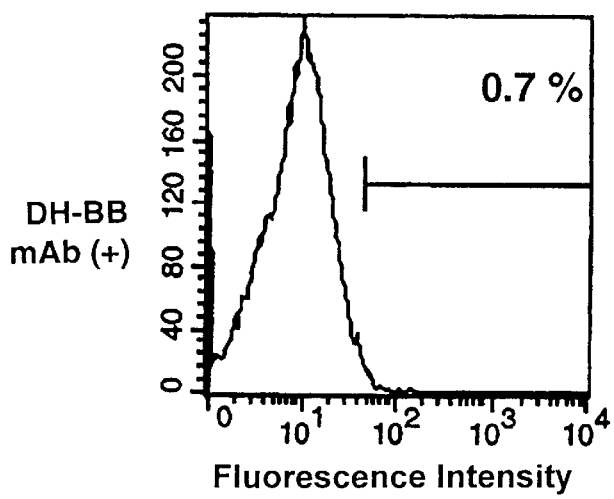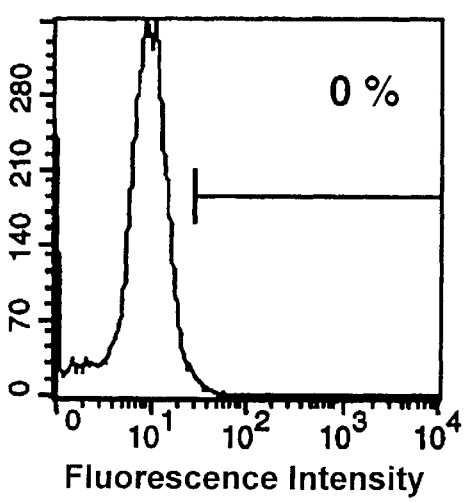
FIG. 6E  FIG. 6F
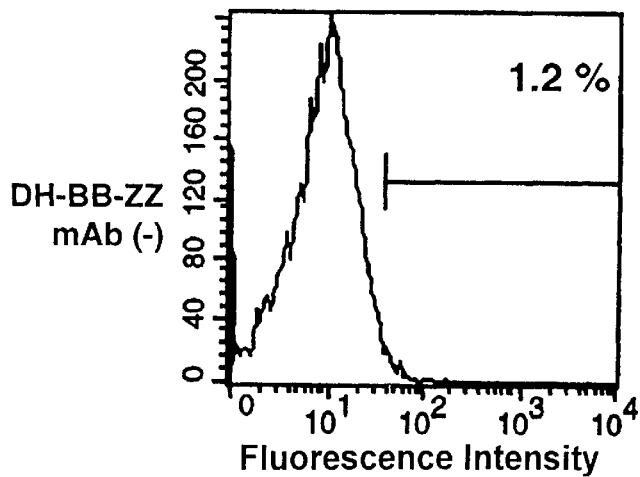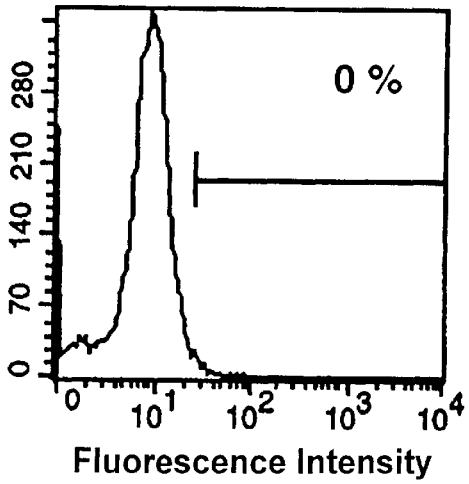
FIG. 6G  FIG. 6H
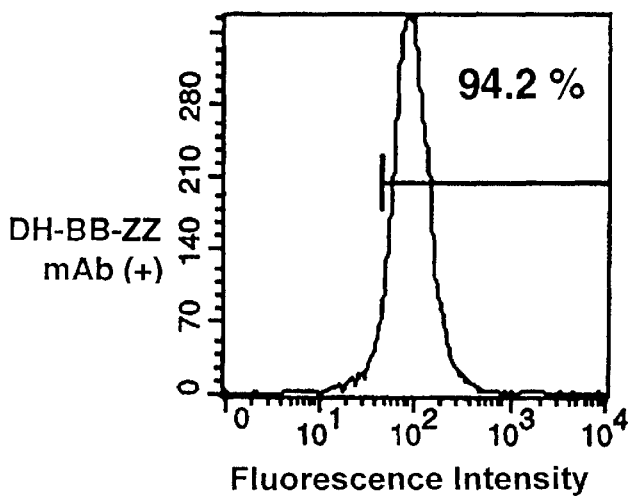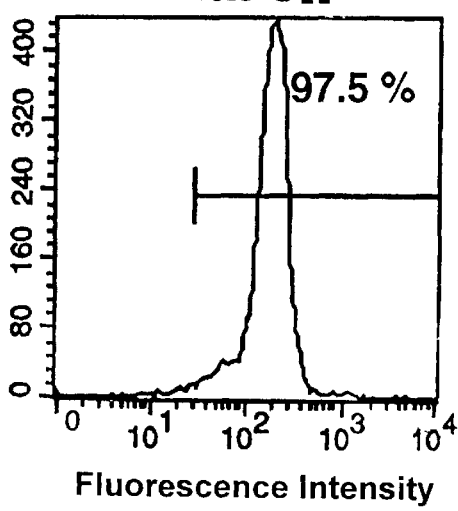
FIG. 6I  FIG. 6J

VIRAL VECTORS HAVING CHIMERIC ENVELOPE PROTEINS CONTAINING THE IGG-BINDING DOMAIN OF PROTEIN A

binds or is bonded to both the viral particle and to the target cell. In one example of this approach, lactose molecules were covalently coupled, by a non-specific reaction, to the envelope proteins of an ecotropic retrovirus, which does not normally infect human cells. A human hepatocellular carcinoma that was known to have receptors for lactose-containing proteins was found to be susceptible to transduction by this vector complex, although the integration of the transduced gene of interest in the target cell chromosome was not directly demonstrated (Neda, H. et al., 1991, *J. Biol. Chem.* 266:14143). No evidence of expression was observed in a hepatocellular carcinoma that lacked the lactose specific receptor. The method of Neda results in a variable number of binding sites for the exposed acceptor-on the target cell, attached to each derivatized or bound envelope protein and, of course, is limited to the case wherein the target cell has a lactose receptor.

Another approach to targeting is the use of adapter molecules involved an adapter that was not covalently coupled to the vector. The use of this type of adapter has been attempted by Roux and his colleagues, who have published several reports that relate to this strategy (Patent Publication FR 2,649,119 to Piecheczyk, Jan. 4, 1991; Roux P. et al., 1989, *Proc. Natl. Acad. Sci.* 86:9079–83; Etienne-Julan, M. et al., 1992, *J. Gen. Virol.* 73:3251–55). Roux and colleagues have constructed adapters from two types of proteins, both typically antibodies, by biotinylating the protein and utilizing avidin or streptavidin tetramer, a protein which binds four biotin molecules, to form aggregates of up to four of the biotinylated proteins.

A better approach is described in U.S. Pat. No. 5,753,499, Meruelo et al., the contents of which are hereby incorporated by reference into this patent application. Meruelo et al. describe viral complexes and methods of use to prepare pre-formed adaptors and linkers suitable for gen therapy. They are particularly well-suited for retroviral systems.

2.3. Use of Sindbis Virus Vectors

Sindbis virus, a member of the Alphavirus genus, has received considerable attention for use as virus-based expression vectors. Many properties of alphavirus vectors make them a desirable alternative to other virus-derived vector systems being developed, including rapid engineering of expression constructs, production of high-titered stocks of infectious particles, infection of nondividing cells, and high levels of expression (Strauss, J. H. et al., 1994, *Microbiol. Rev.* 58:491–562; Liljeström, P. et al., 1991, *Biotechnology* 9:1356–1361; Bredenbeek, P. et al., 1992, *Semin. Virol.* 3:297–310; Xiong, C. et al., 1993, *Science* 243:1188–1191). However, a major drawback to the use of Sindbis virus vectors is the fact that these vectors lack target-cell specificity. For mammalian cells, at least one Sindbis virus receptor is a protein previously identified as the high-affinity laminin receptor, whose wide distribution and highly conserved nature may be in part responsible for the broad host range of the virus (Strauss, J. H. et al. 1994; Wang, K. -S. et al., 1992, *J. Virol.* 66:4992–5001). It is desirable to alter the tropism of the Sindbis virus vectors to permit gene delivery specifically to certain target cell types. This will require both the ablation of endogenous viral tropism and the introduction of novel tropism. In the mature Sindbis virus virion, a plus-stranded viral genome RNA is complexed with capsid protein C to form icosahedral nucleocapsid that is surrounded by lipid bilayer in which two integral membrane glycoproteins, E1 and E2 are embedded (Strauss, J. H. et al., 1994). Although E1 and E2 form heterodimer that functions as a unit, the E2 domain appears to-be particularly important for binding to cells. Monoclonal antibodies (mAbs) capable of neutralizing virus infectivity are usually E2 specific, and mutations in E2, rather than E1, are more often associated with altered host range and virulence (Stanley, J. et al., 1985, *J. Virol.* 56:110–119; Olmsted, R. A. et al., 1986, *Virology* 148:245–254; Polo, J. M. et al., 1988, *J. Virol.* 62:2124–2133; Lustig, S. et al., 1988 *J. Virol.* 62:2329–2336). Recently, a Sindbis virus mutant was identified which contained an insertion in E2 and exhibited defective binding to mammalian cells. This mutant is expected to be useful for development of targetable Sindbis virus vectors (Dubuisson, J. et al., 1993, *J. Virol.* 67:3363–3374).

Grieve et al. (International Publication No. WO 94/17813 published Aug. 18, 1994, "Defective Sindbis Virus Vectors That Express Toxoplasma Gondii P30 Antigens") report the use of defective sindbis viral vectors to protect mammals from protozoan parasites, helminth parasites, ectoparasites, fungi, bacteria and viruses, the contents of which are hereby incorporated by reference. Garoff et al. (International Publication No. WO 92/10578 published Jun. 25, 1992, "DNA Expression Systems Based On Alphaviruses") describe the use of alphaviruses to express protein sequences for immunization or protein production, the contents of which are hereby incorporated by reference. Davis et al. (U.S. Pat. No. 5,185,440 issued Feb. 9, 1993, entitled "cDNA Clone Coding For Venezuelan Equine Encephalitis [(VEE)] Virus And Attenuating Mutations Thereof) disclose cDNA encoding VEE and methods of preparing attenuated Togaviruses, the contents of which are hereby incorporated by reference. Huang et al. (U.S. Pat. No. 5,217,879 issued Jun. 8, 1993, entitled "Infectious Sindbis Virus Vectors") describe infectious Sindbis virus vectors with heterologous sequences inserted into the structural region of the genome, the contents of which are hereby incorporated by reference. Schlessinger et al. (U. S. Pat. No. 5,091,309 issued Feb. 25, 1992, entitled "Sindbis Virus Vectors") describe RNA vectors based on the Sindbis Defective Interfering (DI) particles with heterologous sequences inserted, the contents of which are hereby incorporated by reference. Dalemans et al. (International Publication No. WO 95/27069 published Oct. 12, 1995, "Alpha Virus RNA As Carrier For Vaccines") report the medical use of alphaviruses, specifically the Semliki Forest Virus, to delivery exogenous RNA encoding a antigenic epitope dr determinant, the contents of which are hereby incorporated by reference. Dubensky et al., International Publication No. WO 95/07994 published Mar. 23, 1995, "Recombinant Alphavirus Vectors" describe recombinant retroviral alphavirus vectors for delivery of heterologous genes to target cells, the contents of which are hereby incorporated by reference. Sjöberg et al., International Publication No. WO 95/31565 published Nov. 23, 1995, "Alphavirus Expression Vector" disclose vectors for enhanced expression of heterologous sequences downstream from an alphavirus base sequence, the contents of which are hereby incorporated by reference. Liljeström et al., International Publication No. WO 95/27044 published Oct. 12, 1995, "Alphavirus cDNA Vectors" describe a cDNA construct that may be introduced and transcribed in animal or human cells, the contents of which are hereby incorporated by reference.

3. SUMMARY OF THE INVENTION

The invention concerns viral vectors and their use. Specifically, the invention is concerned with viruses having a protein on the viral particle surface that is a chimeric protein comprising a viral envelope protein and an IgG-binding domain of protein A. Because protein A binds to an Fc region of antibody, these chimeric proteins enable one to use an antibody to target the viral particle to a desired cell to which the antibody binds and not to a cell to which the antibody does not bind.

4. BRIEF DESCRIPTION OF THE FIGURES

Figure 1B:
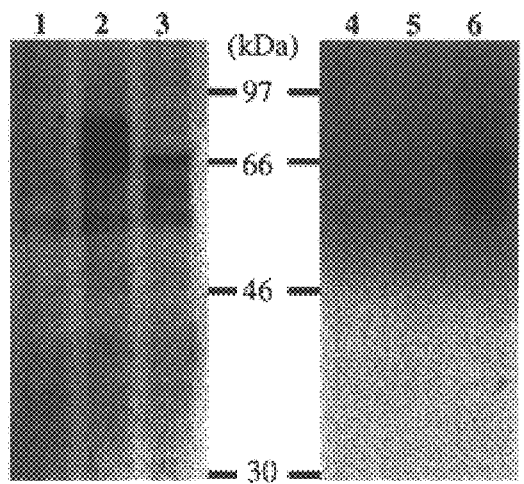

FIG. 1. A. Schematic representation of expression constructs. p439 is the SV40-based expression vector including wild-type M6-MLV envelope gene. Plasmid p439-ZZ was constructed by replacement of the Mo-MLV env gene with synthetic IgG-binding part (ZZ) of protein A between unique restriction sites Bst EII and Bam HI in p439 vector in the presence of compatible linker-spacer. See Materials and Methods for details of construction. Abbreviations: LTR, long terminal repeat ; SV40P, SV40 early enhancer/promoter; L, leader sequence; SU, surface protein; TM, transmembrane protein; ZZ, synthetic protein A; L/S, Linker-Spacer; p(A), polyadenylation signal. B. Immunoblot analysis of lysates from COS-7 cells transiently transfected with p439 and p439-ZZ. Lane 1 and 2 were stained with a SU antiserum followed by HRP-conjugated rabbit anti-goat IgG. Lane 3 and 4 were stained with HRP-conjugated rabbit IgG for detection of protein A.

FIG. 2. A. Immunoblot analysis of virions produced by ψ2 and ψ2-ZZ10 packaging cells. Lane 1 and 2 were stained with a SU antiserum followed by HRP-conjugated rabbit anti-goat IgG. Lane 3 and 4 were stained with HRP-conjugated rabbit IgG for detection of protein A. B. ELISA for detection of IgG-binding activity of chimeric virus produced by ψ2-ZZ10 cells. Open circle, virions from 42; closed circle, virions from ψ2-ZZ10. Results are average of triplicate determinants.

Figure 3A:
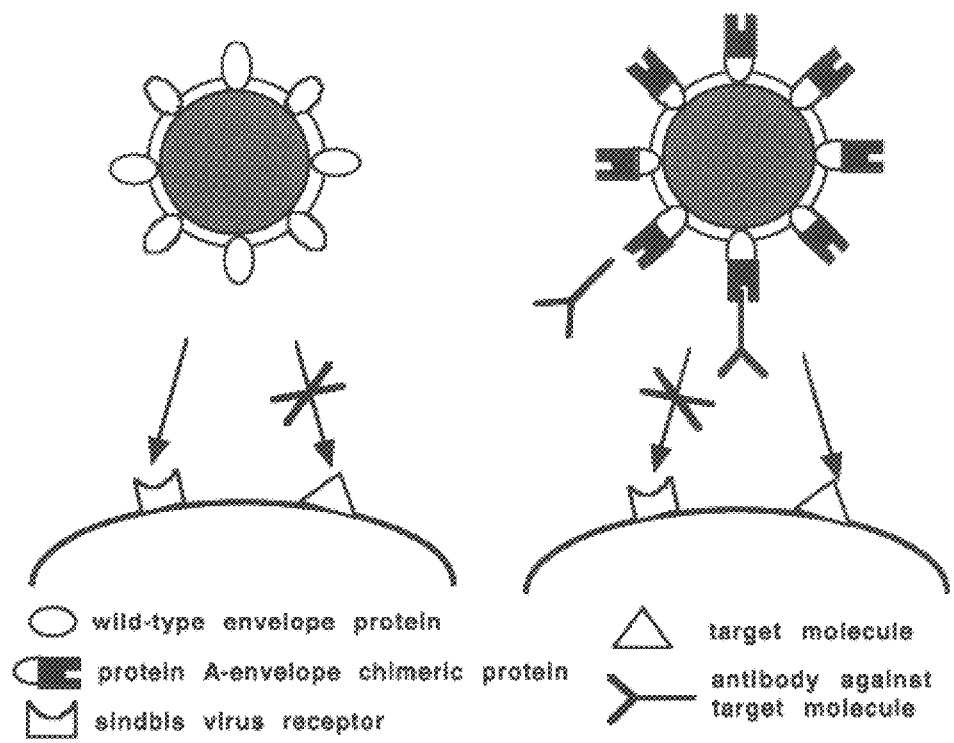

FIG. 3:. (A) Schematic strategy for retargeting an Sindbis virus vector. A wild-type Sindbis virus (left) binds to mammalian cells via its surface receptor which is known to be highly conserved across species. A recombinant Sindbis virus displaying IgG-binding domain of protein A (right) should permit binding to a novel target molecule on the cell surface when used with a corresponding monoclonal antibody (mAb). (B) Schematic representation of recombinant helper constructs and a SinRep/LacZ expression vector. DH-BB is a parental helper plasmid which contains the genes for the structural proteins (capsid, E3, E2, 6K and E1) required for packaging of the Sindbis viral genome. DH-BB-Bst was constructed by introduction of a cloning site (BstEII) into the E2 glycoprotein between amino acids 71 and 74. The synthetic IgG-binding domain (ZZ) of protein A was inserted at BstEII in the DH-BB-Bst helper plasmid and DH-BB-ZZ was obtained. SinRep/LacZ, is a Sindbis virus-based expression vector which contains-the packaging signal, nonstructural protein genes for replicating the RNA transcript and lacZ gene. Abbreviations: $P_{SG}$ Sindbis viral subgenomic promoter; C, capsid; nsP1-4, nonstructural protein genes 1–4; ZZ, synthetic IgG-binding domain of protein A; p(A), polyadenylation signal.

Figure 4A:
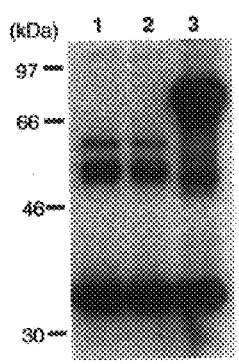

FIG. 4. Detection of Sindbis viral structural protein components and a recombinant envelope. Cell lysates (A) from BHK cells transfected with helper RNA and pellets of viral particles (B and C) produced from these cells were subjected to SDS-PAGE analysis. After transferring to a nitrocellulose filter, viral proteins were stained with diluted anti-Sindbis virus mouse immune ascitic fluid to detect all structural components (A and B) or with HRP-conjugated goat anti-mouse IgG to detect protein A-envelope chimeric protein (C). In each panel, lane 1, DH-BB; lane 2, DH-BB-Bst; lane 3, DH-BB-ZZ.

FIG. 5. Infection of HeLa and HeLa-CD4$^+$ cells with recombinant Sindbis virus derived from DH-BB-ZZ helper RNA which is transducing the bacterial lacZ gene. Viral supernatants (200 μl) were preincubated without or with anti-CD4 mAb (0.5 μg/ml) at room temperature for 1 hour, and added to each cells ($2\times10^5$) in 6-well plates. After 1 hour incubation at room temperature, cells were washed with PBS and incubated in growth medium for 24 hours. Viral infection was evaluated by X-Gal Staining.

FIG. 6. Antibody-dependent infectivities of recombinant Sindbis virus particles on A431 and U87MG cells. Viral supernatants (20 μl for DH-BB, 500 μl for DH-BB-ZZ) were preincubated without or with anti-EGFR mAb (0.5 gg/ml) at room temperature for 1 hour, and added to cells ($2\times10^5$) in 6-well plates. After 1 hour incubation at room temperature, cells were washed with PBS and incubated in growth medium for 24 hours. Viral infection was evaluated by X-Gal Staining.

Figures 7A, 7B, 7C, 7D, 7E:
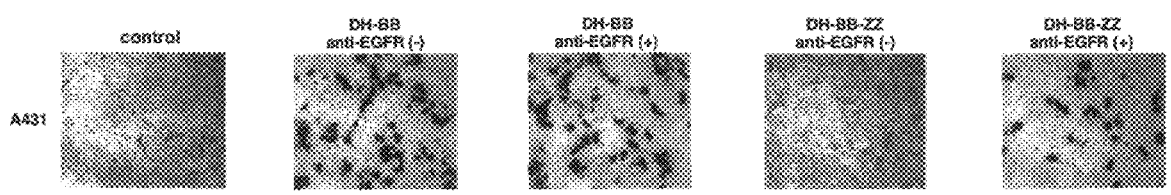
Figures 7F, 7G, 7H, 7I, 7J:
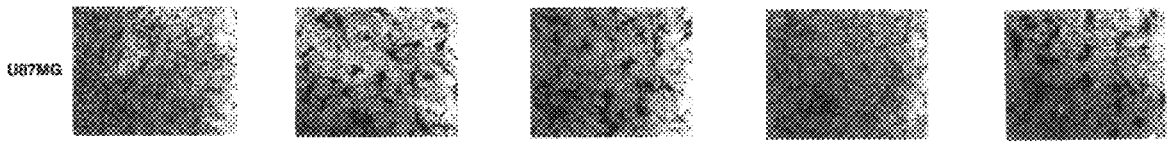

FIG. 7. Antibody-dependent infectivities of recombinant Sindbis virus particles on suspension cells Daudi and HL-60. Viral supernatants (500 μl) derived from DH-BB and DH-BB-ZZ transfected BHK cells were preincubated without or with 0.5 μg/ml of mAbs (anti-HLA-DR for Daudi and anti-CD33 for HL-60) at room temperature for 1 hour, and added to cells ($1\times10^6$) in 6-well plates. After 1 hour incubation at room temperature, cells were washed with PBS and incubated in growth medium for 24 hours. Control shows uninfected cells. Viral infection was evaluated by FACS-Gal analysis described in Experimental protocol. Positive percent of infected cells were shown in each panel.

5. DETAILED DESCRIPTION OF THE INVENTION

The present invention provides for a means for modifying the expression of genes in eukaryotic cells, such as mammalian cells or avian cells, and, more particularly, of human cells for medical practice and also of the cells of domesticated animals that are valuable for agriculture and recreational purposes for veterinary practice. The invention provides for the introduction and expression of genetic material into the cells by means of a viral vector complex. In the viral vector, some or all of the viral genes have been replaced by a gene that is to be expressed in the eukaryotic target cell. The essential viral genes that have been removed from the vector are, in general, inserted into the genome of the cell line that is used to produce stocks of the viral particles. The producer cells lines thus complement the defects that are present in the viral vector. In some embodiments, the only viral gene contained in the genome of the vector is a gene that is needed for the packaging of the vector genome into the viral particles.

Specifically, the invention is directed to viral vectors for transducing a target cell encoding a chimeric protein comprising an envelope protein and an IgG-binding domain of protein A. In one embodiment the envelope protein is a retroviral envelope protein. An example of may be Moloney MLV envelope protein. In the envelope protein is inserted the IgG binding domain of protein A. As used herein, protein A may be a portion of native protein A or synthetic protein having the Fc binding ability of native protein A. In one embodiment it is inserted into the hypervariable region of gp70.

In an alternative embodiment the envelope protein is an alphavirus envelope protein. An example of an alphavirus may be a Sindbis virus. For the Sindbis virus it is preferable to insert the protein A into the E2 domain. The protein A is preferably inserted so as to reduce or minimize the non-specific infectivity of the Sindbis virus. One example of an insertion site is the position between amino acids 71 and 74 of the E2 glycoprotein.

The construction of viral-based vectors suitable for the general expression of genes in cells that are susceptible to infection by the virus is described the following patent publications: WO 89/05345 to Mulligan, R. C. and others, WO 92/07943 to Guild, B. C. and others concerning retroviral vectors; WO 90/09441 and WO 92/07945 to Geller, A. I. and others concerning herpes vectors; WO 94/08026 to Kahn, A. and others, and WO 94/10322 to Herz, J. and others concerning adeno virus vectors; U.S. Pat. No. 5,354,678 to Lebkowski and U.S Pat. No. 5,139,941 to Muzcyzka concerning adeno-associated virus; and U.S. Pat. No. 5,217,879 to Huang et al. and U.S. Pat. No. 5,091,309 to Schlesinger concerning Sindbis viral vectors. Packaging systems for the production of retroviral vectors have been described by Danos, O. et al., 1988, *Proc. Natl. Acad. Sci.* 85:6460–64, and by Landau, N. R. et al., 1992, *J. Virol.* 66:5110–13, the contents of the above are hereby incorporated by reference.

The complexes described herein can be provided with a variety of specificities. The application discloses methods of constructing a complex comprising an antibody specific for an acceptor on the target cell so that the vector complex are internalized into the target cell after the vector complex is bound. There are a large number of cell surface antigens suitable. for use as acceptors and for which antibodies are already available. Such structures include, but are not limited to, the class I and class II Major Histocompatibility Antigens; receptors for a variety of cytokines and cell-type specific growth hormones, brain derived neurotrophic factor (BDNF), ciliary neurotrophic factor (CTNF), colony stimulating growth factors, endothelial growth factors, epidermal growth factors, fibroblast growth factors, glially derived neurotrophic factor, glial growth factors, gro-beta/mip 2, hepatocyte growth factor, insulin-like growth factor, interferons (α-IFN, β-IFN, γ-IFN, consensus IFN), interleukins (IL-1, IL-2, IL-3, IL-4, IL-5, IL-6, IL-7, IL-8, IL-9, IL-10, IL-11, IL-12, IL-13, IL-14), keratinocyte growth factor, leukemia inhibitory factors, macrophage/monocyte chemotactic activating factor, nerve growth factor, neutrophil activating protein 2, platelet derived growth factor, stem cell factor, transforming growth factor, tumor necrosis factors and vascular endothial growth factor; cell adhesion molecules; transport molecules for metabolites such as amino acids; the antigen receptors of B- and T-lymphocytes; and receptors for lipoproteins. The invention makes possible the specific infection of a cell type by allowing the employ of differentiation antigens as targets for the viral vector complex.

The invention is used to transduce a gene of interest into a target cell. In practicing the preferred embodiment of the invention, the viral vector and the antibody are preincubated prior to contacting the target cell acceptor.

The practice of the invention can be performed by culturing the target cells ex vivo. The cultured cells can be continued in culture to produce the product encoded by the transduced gene. Alternatively, the ex vivo transduced cell can be implanted into a subject, which can be the host from which the cultured cells were obtained.

In a yet further embodiment, the viral vector and appropriate antibodies can be administered directly to the subject thereby obviating the need for any ex vivo cell culture. The routes of administration to the subject can be any route that results in contact between the vector complex and the target cell. Thus for example, intravenous administration is suitable for target cells in the hepatic, splenic, renal cardiac and circulatory or hematopoietic systems. The vector complex can also be administered by catheterization of the artery or vein leading to the target organ, thereby allowing the localized administration of the complex. The complex can also be administered by inspiration when the target cells are in the respiratory system.

Genes that can be transduced by the practice of the invention include any gene that can be expressed in a eukaryotic system. Illustrative examples of genes that can be expressed by use of the present invention include glucocerebrosidase, adenosine deaminase, and blood coagulation factors such as factor VIII and factor IX.

The viral component of the vector complex can be based on any virus, the particles of which are unable to bind or have been modified to be unable to bind to cells of the same species as the target cell. A non-limiting example of the virus are the murine ecotropic leukemia retrovirus viruses, e.g., Moloney Leukemia Virus or AKV. Alternatively, chemically modified viral particles can be employed. In addition to ecotropic retroviruses, viruses that can be employed to construct vectors according to this embodiment of the invention include amphotropic retrovirus, herpes virus, adenovirus and adeno-associated virus. In addition, the viral component may be an alphavirus, such as a Sindbis Virus.

The viral vectors and viral complexes of the invention may be used to treat a variety of disorders in man and animals. The vectors based on the Sindbis virus are particularly well suited for intracellular vaccination. That is, the viral complex carries with it a gene of interest encoding a particular antigen. The viral complex will be taken up into the cell and the gene of interest encoding the antigen is will be expressed in the cellular cytoplasm. By targeting the viral complex to desired cellular target, the antigen will be expressed within the cell of interest.

The complexes of this invention are also well suited for the delivery of antisense sequences.

There are many examples of bacterial and viral diseases that may be prevented or ameliorated by the methods described herein. Specifically, the methods described herein may be used for the following diseases: adenovirus, AIDS, antibiotic associated diarrhea, bacterial pneumonia, bovine herpes virus (BHV-1), chlamydia, croup, diphtheria, *Clostridium difficile*, cystitis, cytomegovirus (CMV), gastritis, gonorrhea, heliobactor pyliori, hepatitis A, hepatitis B, herpes virus, HSV-1, HSV-2, human papilloma virus, influenza, legionnaires disease, Lyme disease, malaria, multiple sclerosis, peptic ulcer, pertussis, psoriasis, rabies, respiratory syncytial virus (RSV), rheumatoid arthritis, rhinovirus, rotovirus, salmonella, Stomach cancer, strep throat, tetanus or travelers diarrhea.

The embodiments of the invention are described in greater detail hereinafter.

6. EXAMPLES

6.1. Example 1

In this example we describe the construction of a recombinant ecotropic retrovirus displaying protein A-envelope chimeric proteins. Protein A, a protein derived from *Staphylococcus aureus*, has a strong affinity for the Fc region of various mammalian IgGs (Surolia, A. et al., 1982, *Trends Biochem. Sci.* 7:74–76). Native protein A has five homologous IgG-binding domains (E, D, A, B and C), and we have utilized the synthetic Z domain which is based on the B domain of protein A (Nilsson, B. et al., 1987, *Protein Eng.* 1:107–113). The development of retroviral vectors that can bind IgGs (monoclonal antibodies) would have important applications for specific gene delivery.

Materials and Methods 6.1.1. Plasmids and Cell Line

A SV40-based plasmid, p439 (SV-E-MLV-env), which express Moloney MLV (Mo-MLV) envelope protein (Landau, N. R. et al., 1992, *J. Virol.* 66:5110–5113), was kindly provided Dr. Dan R. Littman, New York University. PEZZ 18, which contains two synthetic Z domains based on the B domain of protein A (Löwenadler, B. et al., 1987, *Gene* 58:87–97) was purchased from Pharmacia Biotech, Uppsala, Sweden. pZeoSV, which has Zeocin-resistant gene for selection, was purchased from Invitrogen Co., San Diego, Calif. An ecotropic retroviral packaging cell line ψ2 (ATCC CRL9560) (Mann, R. et al., 1983, *Cell* 33:153–159) and COS-7 cells (ATCC CRL1651) were maintained in Dulbecco's modified Eagle's medium (DMEM) supplemented with 10% fetal bovine serum (FBS).

6.1.2. Construction of Chimeric Env Gene

Two synthetic IgG-binding domain of protein A (ZZ) were amplified by polymerase chain reaction (PCR) using pEZZ 18 as a template. Primers used for PCR amplification are ZZ-5 (5'-CACGATGAGGTAACCGACAACAAATTCAAC-3') (SEQ ID NO. 1), with Bst EII site, and M13 (−40) sequencing primer (5'-GTTTTCCCAGTCACGAC-3') (SEQ ID NO. 2) which locates downstream from the multiple cloning sites of pEZZ vector. The resulting PCR products were digested with Bst EII and Eco RI and replace[0084] the Mo-MLV env gene between unique restriction sites Bst EII (position 5923) and Bam HI (position 6537) of the p439 vector in the presence of compatible oligonucleotides EB1 (5'-AATTCGGGAGGCGGTGGATCAGGTGGAGGCGGTTCAGG-3') (SEQ ID NO. 3) and EB2 (5'-GATCCCTGAACCGCCTCCACCTGATCCACCGCCTCC-3') (SEQ ID NO. 4) to act as a linker-spacer. Clones containing inserts of proper size were sequenced to confirm that the correct reading frames were maintained.

6.1.3. Cell Transfection and Virus Production

The wild-type and protein A-gp70 chimeric envelope genes were first transiently transfected into COS-7 cells. $2\times10^5$ cells were seeded in 3.5 cm-diameter dishes and transfected the next day with 2 μg of plasmid with 10 μl of LipofectAmine reagent (Gibco-BRL, Gaithersburg, Md.). 72 h after transfection, cells were collected and subjected to immunoblot analysis. To create packaging cell lines expressing the recombinant envelope, $5\times10^5$ ψ2 cells were transfected with 20 μg of chimeric envelope plasmids and 1 μg of pZeoSV by the $CaPO_4$ method (Stratagene, La Jolla, Calif.) (Mann, R. et al., 1983). The medium was changed 16 hours later and transfected cells were selected with 250 μg/ml of Zeocin (Invitrogen Co., San Diego, Calif.) After selection for 10 days, Zeocin-resistant cell colonies were picked for expansion and screened by immunoblot analysis and ELISA as described below.

6.1.4. Immunoblot Assay

For monitoring of protein A-envelope chimeric protein expression, transfected cells and viral samples were subjected to immunoblot analysis. Virus samples were pelleted by ultracentrifugation of the supernatants (10 ml) in an SW41 Beckmann Rotor (25,000 rpm, 2 h, 4° C.). Immunoblot analysis was performed as described before (Marin, M. et al., 1996, *J. Virol.* 70:2957–2962) by using a goat antiserum against Rausher leukemia virus SU protein (Quality Biotech Inc., Camden, N.J.) and horseradish peroxidase-conjugated rabbit anti-goat IgG antibodies (Pierce, Rockford, Ill.).

6.1.5. ELISA

Figure 2A:
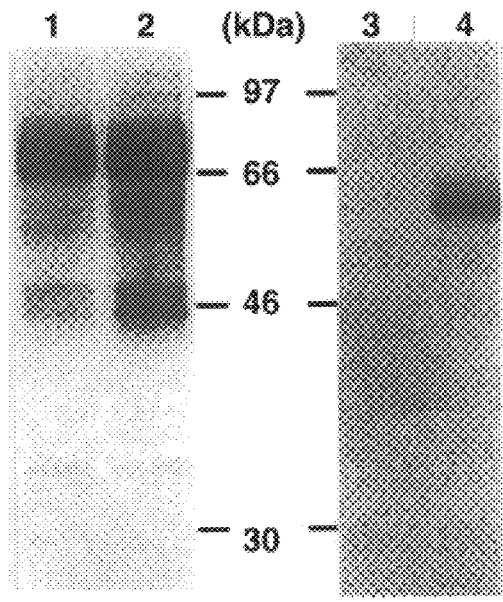
Figure 2B:
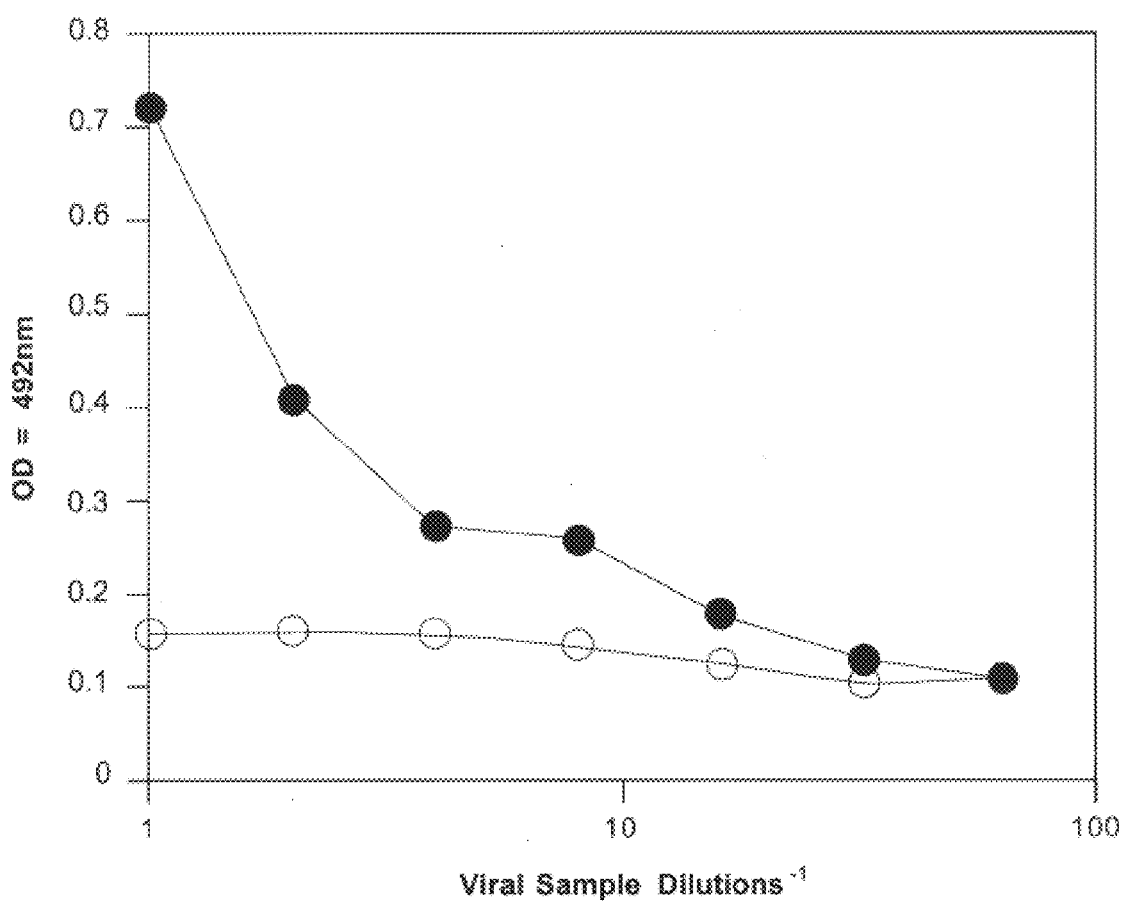

ELISA was performed to detect chimeric virus carrying protein A-envelope chimeric protein in the culture supernatants. Briefly, pelleted viral particles from 10 ml culture supernatants were resuspended in 400 μl of phosphate buffered saline. 96-well microtiter plates (Dynatech Laboratories, INC., Chantilly, Va.) were coated with duplicate serial dilutions of viral samples for 2 h at RT followed by blocking with PBS containing 1% BSA and 0.05% Tween 20. Then 0.1 μ/ml of horseradish peroxidase-conjugated rabbit anti-goat IgG antibodies (Pierce) was added to each well and incubated for 2 h at RT. After washing with PBS containing 0.05% Tween 20, the binding activity of each well was determined by using o-Phenylenediamine (Pierce) as a substrate.

6.1.6. Results

Plasmid Construction and Transient Expression in COS-7 Cells

A modified Mo-MLV envelope expression vector, p439-ZZ, that would express two synthetic IgG-binding domain of protein A was generated (FIG. 1). The position of replacement in gp70 was previously shown to allow the functional display of erythropoietin (Kasahara, N. et al., 1994) and heregulin (Han, X. et al., 1995, *Proc. Natl. Acad. Sci. USA* 92:9747–9751). The C-terminus of the protein A gene is connected to a proline rich hypervariable region of gp70 with the EB linker-spacer (SGGGGSGGGGS) (SEQ ID NO. 5) in order to avoid interactions between the IgG-binding part of protein A and the envelope protein segment of the recombinant fusion protein. Expression is driven by the SV40 early enhancer/promoter sequence and the 5' long terminal repeat (LTR). The plasmid p-439-ZZ was deposited with the American Type Culture Collection (ATCC) on Mar. 28, 1997.

To examine the expression of the recombinant envelope, we transfected p439-ZZ expression plasmid into COS-7 cells. Lysates from transfected and nontransfected cells were first analyzed for envelope expression by using anti-Rauscher leukemia virus SU serum which cross-reacts ecotropic (70 kDa) Mo-MLV SU protein. As expected, the wild-type p439 plasmid expressed major protein bands of gp70 and its precursor (80 kDa) (FIG. 1B, lane 2). The recombinant p439-ZZ plasmid expressed immunoreactive proteins at 70 kDa corresponding to precursor protein of the recombinant envelope suggesting that protein A-gp70 could be expressed in transfected COS cells. The same lysates were used for detection of IgG-binding activity using Horseradish peroxidase-conjugated rabbit anti-goat IgG. As shown in FIG. 1B, lane 6, the protein A-gp70 chimeric envelope precursor at 70 kDa expressed by p439-ZZ plasmid showed IgG-binding activity. Stable expression of the chimeric protein A-gp70 protein suggests that the protein A domain was properly folded after translation.

Creation of Packaging Cell Lines Producing Protein A-envelope Chimeric Virus.

The chimeric envelope plasmid, p439-ZZ, and Zeocin-resistance gene were cotransfected into ψ2 packaging cell line, which expresses gag, pol and env gene products of E-MLV. After selection with Zeocin, subclones were isolated and screened for protein A-gp70 expression by immunoblot analysis of whole cell lysate using rabbit IgG. One subclone, designated ψ2-ZZ10, showed cytoplasmic IgG-binding activity and was chosen for further characterization. To demonstrate the incorporation of the chimeric envelope protein into virions, retroviral particles were purified by sucrose density gradient centrifugation. The viral pellets were then subjected to immunoblot analysis with anti-Rauscher leukemia virus SU serum or rabbit anti-goat IgG. Major bands of 70 kDa, which were derived from wild-type env gene of ψ2 packaging cells, could be detected in both virions from ψ2 and ψ2-ZZ10 cells (FIG. 2A, lane 1 and 2). The band of 60 kDa, which was estimated MW of protein A-gp70 chimeric protein, was also detected in virions produced by ψ2-ZZ10. However, less chimeric envelope was found in virus pellet compared with wild-type envelope. Virions produced by ψ2-ZZ10 showed IgG-binding activity at the band of 60. kDa whereas there was no IgG-binding activity in that of untransfected ψ2 cells (FIG. 2A, lane 3 and 4). The IgG-binding activity of chimeric virus was further confirmed by ELISA. As shown in FIG. 2B, the protein A-envelope chimeric virus produced by ψ2-ZZ10 cells exhibited IgG-binding activity in a concentration dependent manner compared with that of untransfected ψ2 cells. Taken together, these results demonstrate that p439-ZZ produces recombinant retrovirus displaying the IgG-binding domain in its envelope.

6.1.7. Discussion

In this study we have shown that protein A can be displayed on the surface of murine ecotropic retroviral particles fused to the native envelope protein. The protein A-gp70 chimeric protein derived from p439-ZZ was correctly expressed and incorporated into virions. Furthermore, IgG-binding activity was detected in virions produced by ψ2-ZZ10 cells. In this study the chimeric envelope did not express as efficiently as that of wild type envelope in virions produced by ψ2-ZZ10 (FIG. 2A). We are currently trying to increase the expression of protein A-gp70 protein by changing the enhancer/promoter of the expression plasmid as well as utilizing other packaging cell lines.

The use of antibody-antigen interactions as the basis for targeting has a great advantage because a number of monoclonal antibodies have been developed and investigated. Since the protein A portion of the chimeric envelope binds to the Fc domain of the antibody (Surolia, A. et al., 1982), it allows flexibility with regard to the targeting elements, as any of a variety of mAbs can be selected. It has been reported that the binding of retrovirus-associated antibody fragments to the cell surface is followed by membrane fusion between virus and target cells (Etienne-Julan, M. et al., 1992, Roux, P. et al., 1989). The protein A-envelope chimeric retrovirus displaying mAbs against cell surface antigens should bind preferentially to target cells expressing those antigens, and this may facilitate their infection.

Furthermore, in principle, a similar approach may be used with other viral vectors, such as adenovirus and Sindbis virus vectors by inserting the synthetic IgG binding domain (ZZ) of protein A. We also have constructed a recombinant Sindbis virus vector with protein A-envelope and demonstrated its high efficient cell-specific infection against variety of human cells, see Example 2. The protein A-envelope retroviral vector as described in this example should also permit infection against specific cell types once the expression of chimeric envelope successfully increased in the virion. In conclusion, the novel cell targeting system which utilizes protein A-mAb interaction for virus infection would have broad applications for gene expression studies and therapy.

6.2. Example 2

In this example we describe the construction of a recombinant Sindbis virus vector displaying protein A-envelope chimeric proteins to redirect the viral tropism. Protein A (PA), a protein derived from *Staphylococcus aureus*, has a strong affinity for the Fc region of various mammalian IgGs (Surolia, A. et al., 1982). In contrast to the targeted retroviral vectors described above, the PA-envelope chimeric virus vector once successfully generated needs no further modification to target distinct cells. The targeting is achieved simply by changing the complementary mAb (FIG. 3A). More importantly, we demonstrate that this chimeric virus used in conjunction with mAbs can infect human cells and transfer a test gene, bacterial β-galactosidase with high efficiency. The novel cell targeting system which utilizes PA-mAb interaction for virus, infection would have important applications for gene expression studies and therapy.

6.2.1. Results 6.2.2. Construction of Protein A-envelope Sindbis Virus Helper Plasmid To modify the Sindbis virus envelope protein, we have utilized the DH-BB helper plasmid (FIG. 3B) which was constructed by deletion of the region between BspMII and BamHI sites of the full-length Sindbis virus CDNA clone (Bredenbeek, P. J. et al., 1993*, J. Virol*. 67:6439–6446). When RNA from DH-BB is cotransfected with recombinant RNA from the Sindbis virus expression vector (for example, SinRep/LacZ, FIG. 3B), the structural proteins expressed in trans, from the DH-BB RNA transcript allows packaging of the recombinant RNA into virions. Since DH-BB does not contain a packaging signal, it will not form a defective interfering particle or be packaged with recombinant RNA. Two modified Sindbis virus helper plasmids were constructed: DH-BB-Bst into which a BstEII cloning site was inserted and DH-BB-ZZ into which two IgG-binding domain of PA were inserted in the E2 region, were generated (FIG. 3B). Native protein A has five homologous IgG-binding domains (E, D, A, B and C), and we have utilized the synthetic Z domain which is based on the B domain of protein A (Nilsson, B. et al., 1987). The insertion position, between codons 71 and 74 amino acids in E2, was chosen because mutations in this region were previously shown to allow normal particle assembly and release block virus entry at the level of attachment (Dubuisson, J. et al., 1993).

6.2.3. Expression and Incorporation of Chimeric Envelopes into Virions.

After linearization of helper and SinRep/LacZ plasmids, in vitro transcription was performed and the quality of RNA was checked on agarose gels (data not shown). To examine the expression of the recombinant envelope, recombinant helper RNA was cotransfected with RNA from SinRep/LacZ plasmid into BHK cells by electroporation. The transfection efficiency was usually nearly 100% under the procedure described in Experimental protocol below (data not shown). Lysates from transfected cells were first analyzed for expression of structural protein by using anti-Sindbis virus immune ascitic fluid. As shown in FIG. 4A, DH-BB-Bst helper RNA expressed a 50–55 kDa band of envelope (E1 and E2) and a 33 kDa of capsid protein which is the same protein profile as the parental virus produced by DH-BB. A band of 60 kDa corresponding to the E2 precursor PE2 was also detected. In the protein profile expressed by DH-BB-ZZ RNA, a major band between 65–70 kDa, which is the estimated MW of PA-E2 and PA-PE2 chimeric protein, was observed as well as the 33 kDa capsid protein. These results suggest that the mutants were correctly expressed and processed. A band of envelope (E1) looks slightly shifted below in the lysate from DH-BB-ZZ transfected cells due to the disappearance of E2 glycoprotein.

Figure 4B:
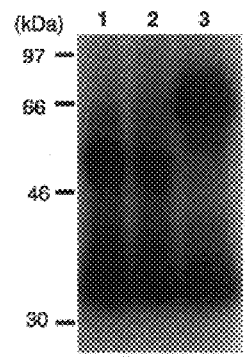
Figure 4C:
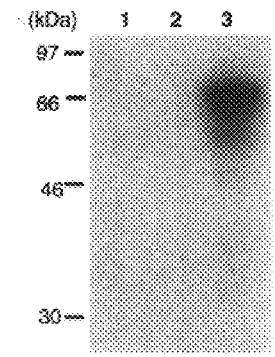
Figure 5A:
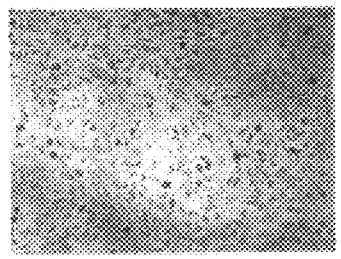
Figure 5B:
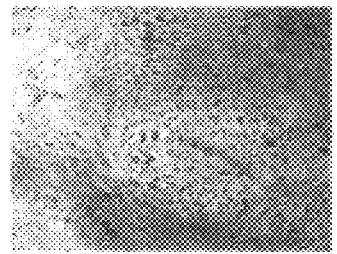
Figure 5C:
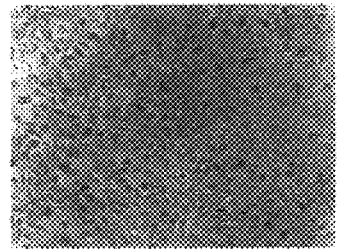
Figure 5D:
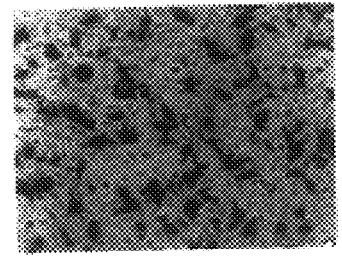

To demonstrate the incorporation of the chimeric envelope protein into virions, viral pellets were subjected to immunoblot analysis. As shown in FIG. 4B, virions produced by DH-BB and DH-BB-Bst RNA contain capsid and envelope (E1 and E2) proteins indicating that the mutation in DH-BB-Bst does not affect virus assembly. The PA-E2 chimeric protein was also incorporated into virions and exhibited IgG-binding activity which is not detected in that of DH-BB and DH-BB-Bst (FIGS. 4B and C). These results demonstrate that DH-BB-ZZ produces recombinant Sindbis pseudovirions displaying the IgG-binding domain in its envelope. The protein band of E1, which was expressed in transfected cells (FIG. 4A, lane 3) could not be detected in the virions produced by DH-BB-ZZ RNA.

6.2.4. Infection with Viruses Carrying Mutant Envelopes

Infectivities of recombinant viruses against hamster and human cells were determined by transfer of the Sindbis virus vector (SinRep/LacZ) that can transduce bacterial β-galactosidase gene. As shown in Table 1, viruses derived from DH-BB and DH-BB-Bst helper showed very high infectious titer ($10^8$ LacZ. CFU/ml) against BHK cells whereas viruses produced by DH-BB-ZZ showed very low infectivity ($10^3$ LacZ CFU/ml) suggesting that the protein A insertion into E2 blocked virus binding to host cells supporting previous observations (Dubuisson, J. et al., 1993). The PA-envelope virus also showed minimal titer against human HeLa-CD4$^+$ cells ($10^2$ LacZ CFU/ml). When virions were preincubated with anti-CD4 mAb, however, the protein A-envelope chimeric virus could infect HeLa-CD4$^+$ cells in a antibody dose-dependent manner (Table 1). When the viral supernatant was preincubated with 0.5 µg/ml mAb, an infectious titer was approximately $10^5$ LacZ CFU/ml. The enhancement of infectivities by mAb was not observed-with that of DH-BB and DH-BB-Bst derived viruses. As shown in FIG. 5, the protein A-envelope chimeric virus with anti-CD4 mAb could not infect HeLa cells which do not express CD4 on its surface indicating that the infection is dependent on both an antibody and a corresponding antigen. These data demonstrate that the PA-E2 chimeric envelope derived from DH-BB-ZZ helper RNA can redirect Sindbis virus infection via a new receptor/antigen in the presence of recognizing antibody.

Next, we determined whether PA-E2 displaying virus particles were capable of infection against various human cell lines expressing specific antigens on their surface. For adherent cells, epidermoid carcinoma cell line A431 and glioblastoma cell line U87MG, both overexpressing epidermal growth factor receptors (EGFR), were used. As expected, viruses with PA-envelope could infect these cells efficiently only when virions were preincubated with anti-EGFR mAb (FIG. 6). Infectious titers of the recombinant virus with mAb (0.5 µg/ml) against A431 and U87MG cells were approximately 10 LacZ CFU/ml. Again, minimal infectivities ($10^2$ LacZ CFU/ml) were seen on these cells when infected without mAb. We next used two human suspension cell lines, Burkitt's lymphoma cells, Daudi, and promyelocytic leukemia cells, HL-60. In this experiment infected cells were detected by FACS-Gal analysis. Typical FACS results of infectivity are presented in FIG. 7. In contrast to the data with adherent cells (FIG. 6), the wild-type virus particles derived from DH-BB helper RNA have very low infectivities against Daudi and HL-60 cells. However, the PA-envelope virus preincubated with corresponding mAbs (anti-HLA-DR for Daudi and anti-CD33 for HL-60) could infect these cells with very high efficiency, and the positive percent of infected cells were more than 90 % in both cell lines. Infection by the protein A-envelope virus of these cells was not observed in the absence of mAb.

6.2.5. Discussion

In this invention we describe the construction of a recombinant Sindbis virus vector displaying protein A-envelope chimeric proteins on the viral surface. The synthetic IgG-binding domain of protein A (ZZ) at the position between 71 and 74 amino acids of the E2 glycoprotein; this site has been shown to block Sindbis virus binding to host cells (Dubuisson, J. et al., 1993). The PA-E2 chimeric protein was correctly expressed and incorporated into Sindbis virions and exhibited IgG-binding activity as shown in FIG. 4B and C. In this experiment, however, the incorporation of E1 glycoprotein into virions could not be detected (FIG. 4C, lane 3) although it is expressed in transfected cells (FIG. 4A, lane 3). Insertion of the IgG-binding domain produces structural change of recombinant E2 chimeric protein that inhibits its interaction with E1 to form a heterodimer. The interaction between E1 and PA-E2 protein is not fully understood. This result also indicates that Sindbis virus assembly may occur without incorporation of the E1 glycoprotein. This observation may provide insight into mechanism of Sindbis virus assembly.

The PA-envelope chimeric Sindbis virus vector showed minimal infectivities against BHK and other human cell lines. However, when used in conjunction with mAbs which react with cell surface antigens, the PA-envelope chimeric virus was able to transfer the LacZ gene into human cell lines with high efficiency. The new tropism of the recombinant virus depends on antigen-antibody interaction since the PA-envelope virus could not infect targeted cells without mAb and corresponding antigen on cell surface (FIG. 5). Taken together, the PA-E2 chimeric envelope derived from DH-BB-ZZ helper RNA can redirect Sindbis virus infection with high efficiency by antigen-antibody interaction.

Several retrovirus and adenovirus-based cell-targeting vectors have been developed recently (Russell, S. J. et al., 1993; Somia, N. V. et al., 1995; Marin, M. et al., 1996; Douglas, J. T. et al., 1996, *Nature, Biotechnology* 14:1574–1578). The novel cell-targeting system developed in this study has some advantages compared with these retroviral and adenoviral retargeting vectors. In this approach it is not necessary to construct each targetable vector de novo. It is unlikely that the incorporation of different targeting elements in the envelope of the virus can always be achieved with equal success and without reducing the virus titers that could be obtained. Since the protein A portion of the chimeric envelope binds to the Fc domain of the antibody (Surolia, A. et al., 1982), it allows flexibility with regards to the targeting elements, as any of a variety of mAbs can be selected. In addition, replication occurs entirely in the cytoplasm of the infected cells as an RNA molecule, without a DNA intermediate (Strauss, J. H. et al., 1994). This is in contrast to retrovirus vectors, which must enter the nucleus and integrate into the host genome for initiation of vector activity. Thus, retrovirus-derived vectors have applications for long-term expression of foreign proteins, while alphavirus vectors are useful primarily for transient high-level expression. Furthermore, although adenovirus vectors can express high levels of foreign proteins, these systems are far more complex than alphaviruses and express many highly antigenic virus-specific gene products including structural proteins (Rosenfeld, M. A. et al., 1991, Science 252:431–434). In contrast, current alphavirus vectors express only the four viral replicase proteins (nonstructural proteins nsP1 through nsP4) required for RNA amplification in the transduced cells.

There are several issue which have to be considered in working with Sindbis vectors. First, Sindbis virus infection of vertebrate cells usually results in cell death by apoptosis (Levine, B. et al. 1993, Nature 361:739–742), with the notable exception of neuronal cells in which a persistent infection may be established (Levine, B. et al. 1992, J. Virol. 66:6429–6435). Although this cytotoxicity may be suitable, for gene therapy for cancer, long-term or inducible expression vectors would have broader application. It has been reported that the transformation of cells with the cellular oncogene bcl-2 led to a cell line in which Sindbis virus no longer induces apoptosis and instead establishes a persistent infection (Levine, B. et al., 1993; Levine, B. et al., 1996, Proc. Natl. Acad. Sci. USA 93:4810–4815, the contents of which are hereby incorporated by reference into the present application). bcl-2 may be used to construct a long-term Sindbis virus expression vector that overcomes the problems of apoptosis. The bcl-2 vector would be particularly well suited to create a master packaging cell line also expressing the both chimeric Sindbis envelop protein and a heterologous gene of interest under the control a Sindbis promotor. Second, the recombinant Sindbis virus vector developed in this invention may have low infectivities even in the absence of antibody. Accordingly, there might be other sites in E2 or E1 which are involved in receptor binding (Strauss, J. H. et al., 1994). Furthermore, different receptors have been identified on chicken embryo fibroblast (Wang, K. S. et al., Virology 181:694–702) and mouse neuronal cells (Ubol, S. et al., 1991, J. Virol. 65:6913–6921), suggesting that the Sindbis virus can utilize more than one receptor. For safety reason, it is desirable to develop improved: recombinant Sindbis virus vector which do not infect any mammalian cells when not used with mAbs.

This invention represents the first demonstration of the retargeting of a Sindbis virus vector by a novel utilization of the protein A-antibody interaction. A similar approach may be used with other viral vectors, such as retrovirus and adenovirus vectors by inserting the synthetic IgG binding domain (ZZ) of protein A. The virus-based vectors displaying protein A-envelope could be very useful and have a broad applicability for gene transfer study and for the gene therapy field.

6.2.6. Experimental Protocol

Cell lines. Baby hamster kidney (BHK) cells were obtained from Invitrogen Co., San Diego, Calif., and maintained in minimum essential medium alpha-modification (αMEM, JRH Biosciences, Lenexa, Kans.) supplemented with 5% fetal bovine serum (FBS, Gemini Bio-Products, Inc., Calabasas, Calif.). A human epidermoid carcinoma cell line A431 (ATCC CRL1555), a human epitheloid carcinoma cell line HeLa (ATCC CRL2) and a human glioblastoma cell line U87MG (ATCC HTB14) were grown as monolayers in Dulbecco's modified Eagle's medium (DMEM; GIBCO-BRL, Gaithersburg, Md.) supplemented with 10% FBS.

HeLa $CD4^+$ Clone 1022 (NIH AIDS Research and Reference Reagent Program), which express CD4 on their surface and a human Burkitt's lymphoma cell line Daudi (ATCC CCL213), (ATCC CRL1582) was maintained in RPMI 1640 (JRH Bioscience) supplemented with 10% FBS. HL-60, promyelocytic leukemia cell line (ATCC CCL240), was maintained in RPMI 1640 supplemented with 20% FBS.

Monoclonal antibodies (mAbs). A murine mAb of IgG2a type against the human epidermal growth factor receptor (EGFR) was obtained from Upstate Biotechnology (Lake Placid, N.Y.). Anti-HLA-DR (mouse IgG2a), anti-CD4 (mouse IgGi) and anti-CD33 (mouse IgG1) were purchased from Becton Dickinson (San Jose, Calif.).

Plasmids. A helper plasmid DH-BB (Invitrogen Co., FIG. 1B) (Bredenbeek, P. J. et al., 1993) which contains the genes for the structural proteins (capsid, E3, E2, 6K and E1) required for packaging of the Sindbis viral genome was used for construction of the recombinant envelope gene. A Sindbis virus-based expression vector SinRep/LacZ (Invitrogen Co., FIG. 3B) (Bredenbeek, P. J. et al., 1993) contains the packaging signal, nonstructural protein genes 1-4 (nsP1-4) for replicating the RNA transcript and the lacZ gene. Plasmid pEZZ 18, which contains two synthetic Z domains based on the B domain of protein A (Löwenadler, B. et al., 1987), was purchased from Pharmacia Biotech, Uppsala, Sweden. The phagemid pALTER-1 vector (Promega Co. Madison, Wis.) was used to introduce the BstEII site in E2 region of DH-BB plasmid by oligo-directed site-specific mutagenesis.

Figure 3B:
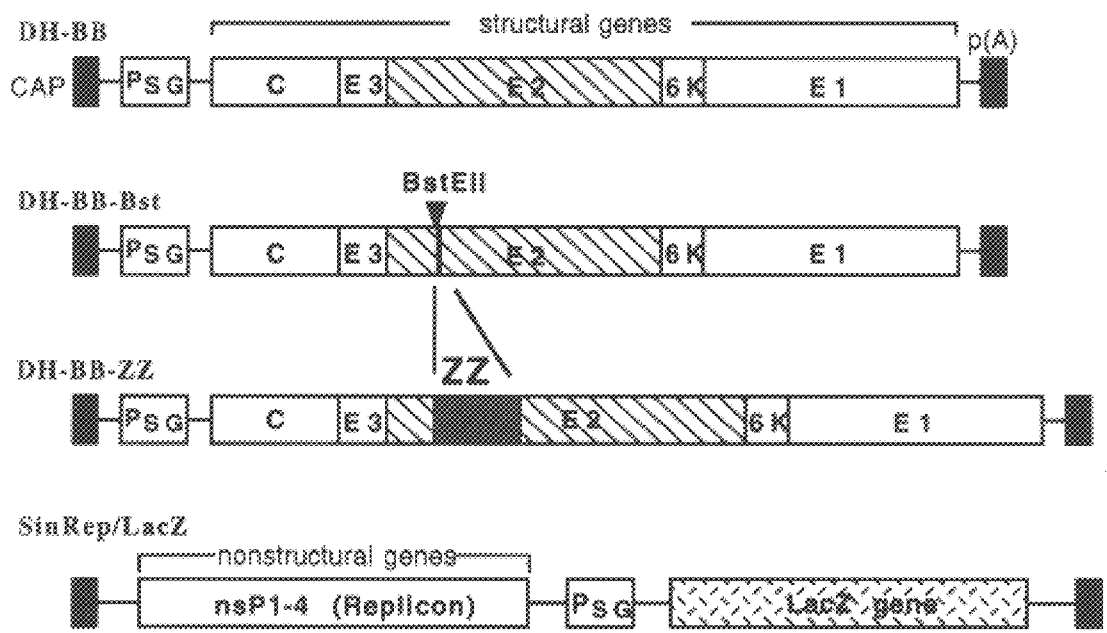

Construction of the recombinant Sindbis virus structural gene. Altered Sites in vitro Mutagenesis System (Promega Co.) 10 was used to introduce a specific restriction site into the E2 region of Sindbis virus structural gene. First, a BssHII site was introduced between XbaI and HindIII sites of the pALTER-1 vector by using two compatible oligonucleotides 5'-CTAGAGCGCGCAAA-3' and 5'-AGCTTTTGCGCGCT-3' (SEQ ID NOS. 6–7). A fragment between SacI and BssHII of the DH-BB plasmid containing the E2 region of structural gene was cloned into the pALTER-1 vector. A single-stranded template of the recombinant pALTER-1 vector was prepared by infection of helper phage M13KO7. A mutagenic oligonucleotide (5'-ATGTCGCTTAAGCAGGTAACCACCGTTAAAGAA GGC-3') (SEQ ID NO. 8) which introduces a BstEII cloning site between codons 71 and 74 amino acids in E2 polypeptides and an ampicillin repair oligonucleotide (5'-GTTGCCATTGCTGCAGGCATCGTGGTG-3') (SEQ ID NO. 9) were annealed to the single-stranded template, followed by synthesis of the mutant strand with T4 DNA polymerase. After transformation into E. coli, mutants were selected in the presence of ampicillin and screened by direct sequencing of the plasmid DNA. The SacI-BssHII region of original DH-BB plasmid was replaced with the mutated fragment and the DH-BB-Bst plasmid was obtained (FIG. 3B). A region of protein A (ZZ) containing two synthetic IgG-binding domain was amplified by the polymerase chain reaction (PCR) using pEZZ 18 as a template. Primers used for PCR amplification are ZZ-5 (5'-CACGATGAGGTAACCGACAACAAATTCAAC-3') and ZZ-3 (5'-GGTCGAGGTTACCGGATCCCCGGGTACCGA-3') (SEQ ID NOS. 10–11) both encoding unique BstEII sites. The resulting PCR products were digested-with BstEII and inserted into predigested DH-BB-Bst plasmid at the BstEII site. Clones containing inserts of proper size and orientation were sequenced to confirm that the correct reading frames were maintained and the DH-BB-ZZ plasmid was obtained (FIG. 3B). The plasmid p-DH-BB-ZZ was deposited with the American Type Culture Collection (ATCC) on Mar. 28, 1997.

In vitro transcription and transfection for recombinant virus production. Plasmids for in vitro transcription were prepared by use of Qiagen (Chatsworth, Calif.) columns. All helper plasmids (DH-BB, DH-BB-Bst and DH-BB-ZZ) and SinRep/LacZ plasmid were linearized by XhoI restriction enzyme digestion and purified by phenol/chloroform extraction followed by ethanol precipitation. Transcription reactions were carried out by using InvitroScript Cap Kit (Invitrogen Co.) to produce large quantities of capped mRNA transcript from the SP6 promoter. For cotransfections of helper and SinRep/LacZ RNA into BHK cells, electroporations were performed as described before (Liljeström, P. et al., 1991, Biotechnology 9:1356–1361). Electroporated cells were transferred to 10 ml of αMEM containing 5% FCS and incubated for 12 hours. Cells were then washed with PBS and incubated in 10 ml of Opti-MEM I medium (GIBCO-BRL) without FCS. After 24 hours, culture supernatants were harvested and aliquots were stored at −80° C.

Immunoblot assay. Cells were lysed in 20 mM Tris-HCl buffer (pH 8.0) containing 1% Triton X, 0.15 M NaCl, 1 mM phenylmethylsulfonyl fluoride, 1 mM EDTA and 10% glycerol 24 hour after transfection. Cell extracts were then sonicated and mixed with electrophoresis loading buffer (125 mM Tris-HCl, pH 6.8, 10 mM β-mercaptoethanol, 2% SDS, 10% glycerol and 0.01% bromphenol blue). Virus samples were pelleted by ultracentrifugation of the supernatants (10 ml) in an SW41 Beckmann Rotor (35,000 rpm, 2 h, 4° C.) and resuspended in electrophoresis loading buffer. Cell extracts and viral samples were subjected to immunoblot analysis as described before (Marin, M. et al., 1996) by using anti-Sindbis virus mouse immune ascitic fluid (ATCC VR-1248) and horseradish peroxidase (HRP)-conjugated rabbit anti-goat IgG antibodies (Pierce, Rockford, Ill.).

Infection assays. Infectivity of recombinant chimeric viruses to BHK and human cell lines was determined by transfer of the Sindbis virus vector (SinRep/LacZ) that can transduce the bacterial β-galactosidase gene (Bredenbeek, P. J. et al., 1993). Viral supernatant dilutions were incubated with or without monoclonal antibodies at room temperature for 1 hour, then added to adherent ($2 \times 10^5$) and suspension ($1 \times 10^6$) cells in 6-well plates. After 1 hour incubation at room temperature, cells were washed with PBS and incubated in growth medium for 24 hours. Viral infection was evaluated by X-Gal Staining and FACS-Gal as described below and titers were estimated in LacZ CFU per milliliter.

X-Gal staining and FACS-Gal Assay. For X-gal staining, commercial protocol was followed. Briefly, cells were fixed in PBS containing 0.5% glutaraldehyde for 15 min followed by washing with PBS three times. Then cells were stained with PBS containing 1 mg/ml X-gal, 5 mM potassium ferricyanide, 5 mM potassium ferrocyanide and 1 mM $MgSO_4$ at 37° C. for 2 hours. The FACS-Gal assays were performed as described previously (Fiering, S. N. et al., 1991, Cytometry 12:291–301).

The present invention is not to be limited in scope by the specific embodiments described which were intended as single illustrations of individual aspects of the invention, and functionally equivalent methods and components were within the scope of the invention. Indeed, various modifications of the invention, in addition to those shown and described herein will become apparent to those skilled in the art from the foregoing description and accompanying drawings. Such modifications are intended to fall within the scope of the appended claims.

7. DEPOSIT OF MICROORGANISMS

The following organisms were deposited with the American Type Culture Collection (ATCC), 10801 University Boulevard, Manassa, Va. 20110-2209 on Mar. 28, 1997.

| Strain Designation | Containing | Accession No. |
| --- | --- | --- |
| p-439-ZZ | Expression plasmid | 98378 |
| p-DH-BB-ZZ | Expression plasmid | 98377 |

---

We claim:

1. A Sindbis viral vector for transducing a target cell with high efficiency which comprises a gene encoding a chimeric envelope protein containing an IgG-binding domain of protein A sufficient to bind an Fc domain of an antibody with strong affinity wherein the envelope protein is a Sindbis virus envelope protein; wherein the envelope protein is operable to direct the assembly of the protein into a viral particle; and wherein said chimeric envelope protein alters natural viral tropism.

2. The viral vector of claim 1, wherein the portion of the IgG binding domain of Protein A is inserted into an E2 glycoprotein of the Sindbis virus envelope protein.

3. The viral vector of claim 2, wherein the envelope protein consists essentially of a fusion protein of an E2 glycoprotein of the Sindbis virus-envelope protein and the IgG-binding domain of protein A.

4. A packaging cell which comprises the viral vector of claim 1.

5. The packaging cell of claim 4, wherein the virus is an alphavirus and the packaging cell(further comprises a heterologous gene encoding bcl-2.

6. The packaging cell of claim 5, wherein the packaging cell is an ecotropic cell.

7. The packaging cell of claim 4, wherein the packaging cell is an ecotropic cell.

8. The packaging cell of claim 4, wherein the ecotropic packaging cell is a $\psi 2$ packaging cell.

9. A chimeric Sindbis virus for transducing a target cell with high efficiency which comprises a gene of interest under the control of an appropriate viral sequence and a chimeric protein comprising a chimeric Sindbis envelope protein containing an IgG-binding domain of protein A sufficient to bind an Fc domain of an antibody with strong affinity and wherein said chimeric envelope protein alters natural viral tropism.

10. The chimeric virus of claim 9, wherein the IgG binding domain is expressed on the surface of the envelope protein.

11. The chimeric virus of claim 9 wherein the virus further comprises an antibody targeting a particular cell of interest.

12. The chimeric virus of claim 11 wherein the antibody binds to a receptor for a cytokine, which cytokine is selected from the group consisting of brain derived neurotrophic factor, ciliary neurotrophic factor, colony stimulating growth factors, endothelial growth factors, epidermal growth factors, fibroblast growth factors, glially derived neurotrophic factor, glial growth factors, gro-beta/mip 2, hepatocyte growth factor, insulin-like growth factor, interferons, interleukins, keratinocyte growth factor, leukemia inhibitory factors, macrophage/monocyte chemotactic activating factor, nerve growth factor, neutrophil activating protein 2, platelet derived growth factor, stem cell factor, transforming growth factor, tumor necrosis factors and vascular endothelial growth factor.

13. The chimeric virus of claim 11 in which the antibody binds an antigen which is selected from the group consisting of class I MHC antigens, class II MHC antigens, internalizing cell-surface receptors and viral receptors.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

CACGATGAGG TAACCGACAA CAAATTCAAC              30

(2) INFORMATION FOR SEQ ID NO:2:

(i) SEQUENCE CHARACTERISTICS:

(A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

GTTTTCCCAG TCACGAC                                                        17

(2) INFORMATION FOR SEQ ID NO:3:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

AATTCGGGAG GCGGTGGATC AGGTGGAGGC GGTTCAGG                                  38

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GATCCCTGAA CCGCCTCCAC CTGATCCACC GCCTCC                                   36

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:5:

Ser Gly Gly Gly Gly Ser Gly Gly Gly Gly Ser
 1               5                  10

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CTAGAGCGCG CAAA                                                           14

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single -continued (D) TOPOLOGY: linear (ii) MOLECULE TYPE: DNA (xi) SEQUENCE DESCRIPTION: SEQ ID NO:7:

AGCTTTTGCG CGCT                                                                14

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

ATGTCGCTTA AGCAGGTAAC CACCGTTAAA GAAGGC                                         36

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GTTGCCATTG CTGCAGGCAT CGTGGTG                                                   27

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CACGATGAGG TAACCGACAA CAAATTCAAC                                                30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GGTCGAGGTT ACCGGATCCC CGGGTACCGA                                                30